(12) United States Patent
Dos Santos et al.

(10) Patent No.: US 8,585,664 B2
(45) Date of Patent: Nov. 19, 2013

(54) SYSTEM AND METHOD FOR POWERING OCULAR IMPLANTS

(75) Inventors: Cesario P. Dos Santos, Aliso Viejo, CA (US); Daniel C. Jenkins, Pomona, CA (US)

(73) Assignee: Alcon Research, Ltd, Fort Worth, TX (US)

( * ) Notice: Subject to any disclaimer, the term of this patent is extended or adjusted under 35 U.S.C. 154(b) by 0 days.

(21) Appl. No.: 13/316,660

(22) Filed: Dec. 12, 2011

(65) Prior Publication Data
US 2013/0150771 A1 Jun. 13, 2013

(51) Int. Cl.
*A61M 5/00* (2006.01)
*A61M 35/00* (2006.01)

(52) U.S. Cl.
USPC .................................. 604/294; 604/8; 606/6

(58) Field of Classification Search
USPC ........................................ 604/8–10; 606/4–6
See application file for complete search history.

(56) References Cited

U.S. PATENT DOCUMENTS

2011/0071454 A1* 3/2011 Dos Santos et al. .............. 604/8

* cited by examiner

*Primary Examiner* — Melanie Hand
(74) *Attorney, Agent, or Firm* — Kenneth D. Bassinger

(57) ABSTRACT

A system for treating an ocular condition of a patient includes an electrically powered ocular implant sized for placement within an eye and includes a transmitter sized to be carried on or adjacent the head of the patient for disposal adjacent the eye. The transmitter includes a transmission antenna that emits an electromagnetic flux field sufficient to energize the ocular implant and includes a flux shunt disposed within the electromagnetic flux field. The transmission antenna may be disposed between the flux shunt and the implant.

20 Claims, 3 Drawing Sheets

SYSTEM AND METHOD FOR POWERING OCULAR IMPLANTS

BACKGROUND

The present disclosure relates generally to systems and methods for powering ocular implants for use in ophthalmic treatments.

Glaucoma, a group of eye diseases affecting the retina and optic nerve, is one of the leading causes of blindness worldwide. Most forms of glaucoma result when the intraocular pressure (IOP) increases to pressures above normal for prolonged periods of time. IOP can increase due to high resistance to the drainage of the aqueous humor relative to its production. Left untreated, an elevated IOP causes irreversible damage to the optic nerve and retinal fibers resulting in a progressive, permanent loss of vision.

FIG. 1 is a diagram of the front portion of an eye that helps to explain the processes of glaucoma. In FIG. 1, representations of the lens 110, cornea 120, iris 130, ciliary body 140, trabecular meshwork 150, and Schlemm's canal 160 are pictured. Anatomically, the anterior segment of the eye includes the structures that cause elevated IOP which may lead to glaucoma. Aqueous fluid is produced by the ciliary body 140 that lies beneath the iris 130 and adjacent to the lens 110 in the anterior segment of the eye. This aqueous humor washes over the lens 110 and iris 130 and flows to the treatment system located in the angle of the anterior chamber. The angle of the anterior chamber, which extends circumferentially around the eye, contains structures that allow the aqueous humor to drain. The trabecular meshwork 150 is commonly implicated in glaucoma. The trabecular meshwork 150 extends circumferentially around the anterior chamber. The trabecular meshwork 150 seems to act as a filter, limiting the outflow of aqueous humor and providing a back pressure that directly relates to IOP. Schlemm's canal 160 is located beyond the trabecular meshwork 150. Schlemm's canal 160 is fluidically coupled to collector channels (not shown) allowing aqueous humor to flow out of the anterior chamber. The two arrows in the anterior segment of FIG. 1 show the flow of aqueous humor from the ciliary bodies 140, over the lens 110, over the iris 130, through the trabecular meshwork 150, and into Schlemm's canal 160 and its collector channels.

One method of treating eye disease such as glaucoma includes implanting a treatment device in a patient's eye. Such a treatment devices can allow fluid to flow from the interior chamber of the eye to a drainage site, relieving pressure in the eye and thus lowering IOP. These devices however, are passive, unpowered devices and therefore, do not allow monitoring or interactive control of the treatment device. Therefore, responding to particular conditions does not occur.

Accordingly, there exists a need for a powered system or implant that may be utilized to treat eye diseases such as glaucoma for example. The system and methods disclosed herein overcome one or more of the deficiencies of the prior art.

SUMMARY

In one exemplary aspect, the present disclosure is directed to a system for treating an ocular condition of a patient. The system includes an ocular implant sized for placement within an eye. The implant includes an electrically powered treatment element and an antenna configured to receive energy for operating the electrically powered treatment element. The system also includes a wearable external system that includes a transmitter sized to be carried on or adjacent the head of the patient for disposal adjacent the eye. The transmitter is arranged to emit an electromagnetic flux field sufficient to energize the antenna and provide power to operate the electrically powered treatment element of the implant. A power source is in communication with the transmitter and configured to provide power to the transmitter to emit the electromagnetic flux field. In one aspect, the transmitter includes a transmission antenna that emits the electromagnetic flux field and includes a flux shunt disposed within the electromagnetic flux field. The transmission antenna may be disposed between the flux shunt and the implant.

In another exemplary aspect, the present disclosure is directed to a system for treating an ocular condition of a patient. The system includes an electrically powered ocular implant sized for placement within an eye and includes a transmitter sized to be carried on or adjacent the head of the patient for disposal adjacent the eye. The transmitter includes a transmission antenna that emits an electromagnetic flux field sufficient to energize the ocular implant and includes a flux shunt disposed within the electromagnetic flux field. The transmission antenna may be disposed between the flux shunt and the implant.

In one aspect, the flux shunt is cylindrically shaped and has a longitudinal axis extending in substantially the same direction as the transmitter. In another aspect, the flux shunt is disposed at a location relative to the transmission antenna that reduces the electromagnetic flux field in a direction away from the ocular implant.

In yet another exemplary aspect, the present disclosure is directed to a method of powering an ocular implant sized for implantation in an eye of a patient. The method includes generating an electromagnetic flux field with a transmitter worn by the patient and disposed at a location relative to the ocular implant so that the electromagnetic flux field encompasses the implant. The method also includes limiting the electromagnetic flux field in a direction away from the implant in a manner that increases the electromagnetic flux field in a direction toward the implant. It also includes receiving energy at the implant from the electromagnetic flux field to power an electrically driven element on the implant to treat an ocular condition. In one aspect, generating an electromagnetic flux field with a transmitter comprises generating the field with a transmission antenna, and limiting the electromagnetic flux field in a direction away from the implant comprises locating a flux shunt at a side of the transmission antenna away from the implant.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTION OF THE DRAWINGS

The accompanying drawings illustrate embodiments of the devices and methods disclosed herein and together with the description, serve to explain the principles of the present disclosure.

DETAILED DESCRIPTION OF THE PREFERRED EMBODIMENTS

Figure 1:
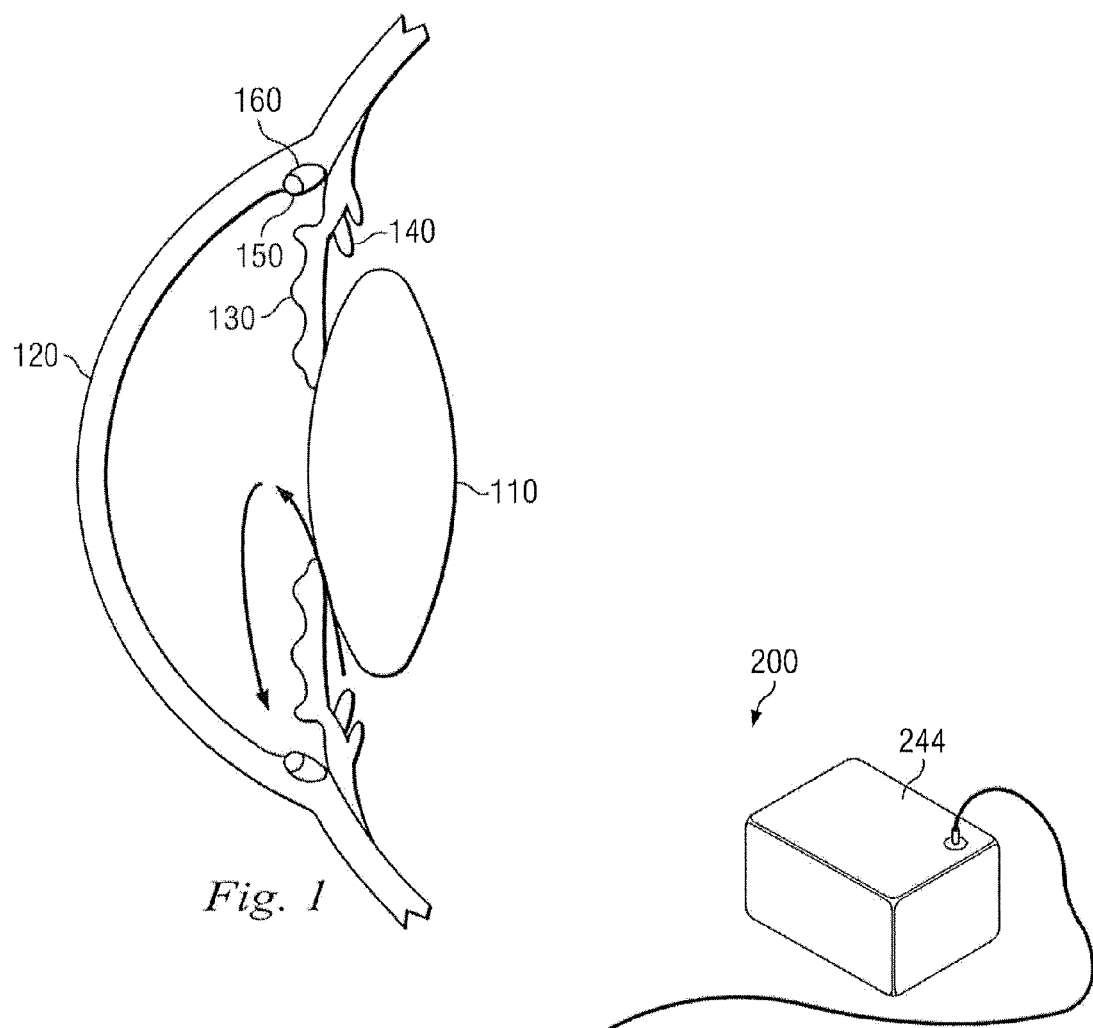
FIG. 1 is a diagram of the front portion of an eye.

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For simplicity, in some instances the same reference numbers are used throughout the drawings to refer to the same or like parts.

The present disclosure is directed to a system and method of providing power to an intraocular implant. In at least one aspect, an external system transmits a wireless electromagnetic field to the implant. The system operates to direct more of the electromagnetic field toward the implant and less of the electromagnetic field in directions away from the implant. An exemplary embodiment herein uses a shunting technique to shape a field contour density that directs the electromagnetic field toward the implant. A particular implant is designed to receive and store power for operation during a non-charging state.

Figure 2:
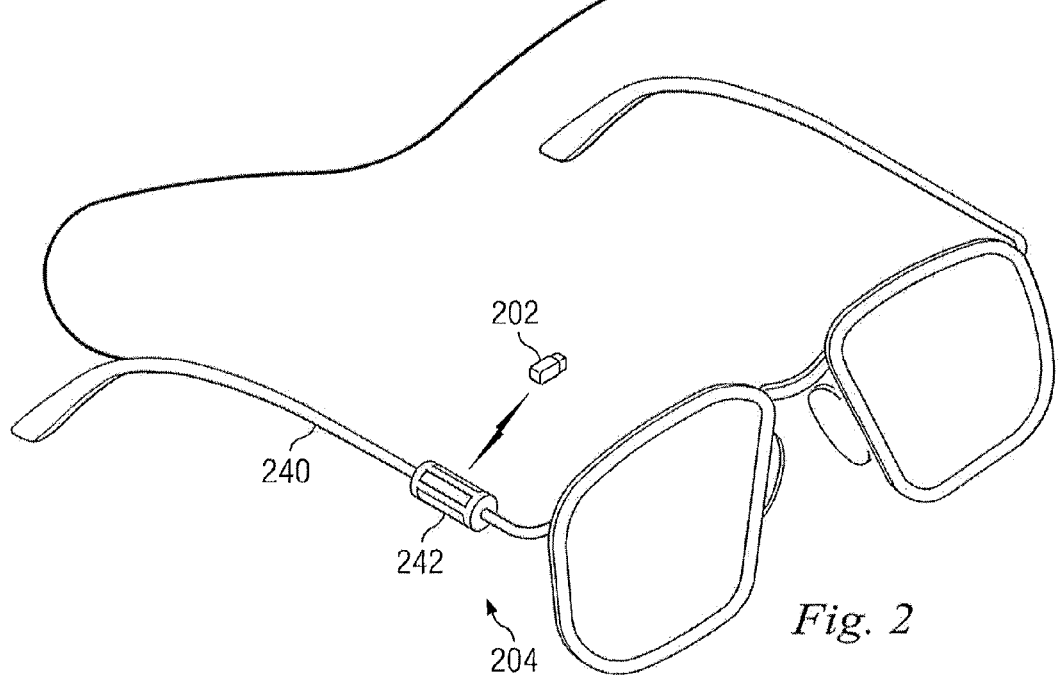
FIG. 2 is a schematic diagram of an exemplary of an ocular treatment system according to an exemplary embodiment of the present disclosure.

FIG. 2 shows an exemplary ocular treatment system 200 including an implant 202 and an external unit 204. The implant 202 includes a powered treatment element that may be used to monitor or treat an ocular condition, such as glaucoma, for example. The external unit 204 is configured to provide power to the implant 202 as well as communicate with it. As explained below, this is accomplished via a wireless link where the external unit 204 transmits an electromagnetic field into the volume occupied by the implant 202. The implant 202 captures and uses energy from the electromagnetic field as an energy source and as a carrier wave to be modulated for half-duplex communications. The implant 202 will be described first, followed by a description of the external unit 204.

Figure 3:
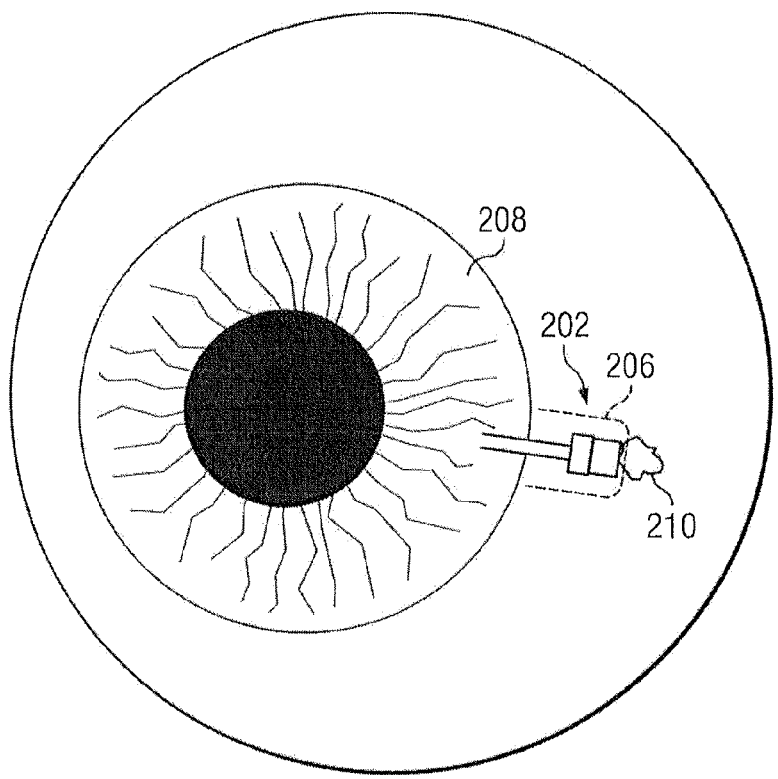
FIG. 3 is a schematic diagram of an implant of the ocular treatment system disposed in an eye of a patient according to an exemplary embodiment of the present disclosure.

FIG. 3 is a diagram of one possible application of the implant 202 shown implanted in the eye. In this example, the implant 202 is sized and arranged to be implanted in the subconjunctival pocket 206 of the eye. In one example, the implant may be arranged to shunt fluid from an anterior chamber 208 to a drainage site 210, which may be at any of numerous locations within the eye in order to treat glaucoma by maintaining or achieving a desired IOP. For example, some implants are arranged to shunt aqueous from the anterior chamber 208 to the subconjunctival space or, alternatively, to the subscleral space. Other implants shunt aqueous humor from the anterior chamber to the suprachoroidal space, the supraciliary space, the juxta-uveal space, or to the choroid. In yet other applications, the implant 202 shunts aqueous humor from the anterior chamber 208 to Schlemm's canal, a collector channel in Schlemm's canal, or any of a number of different blood vessels like an episcleral vein. In some examples, the implant even shunts aqueous humor from the anterior chamber 208 to outside the conjunctiva.

Figure 4:
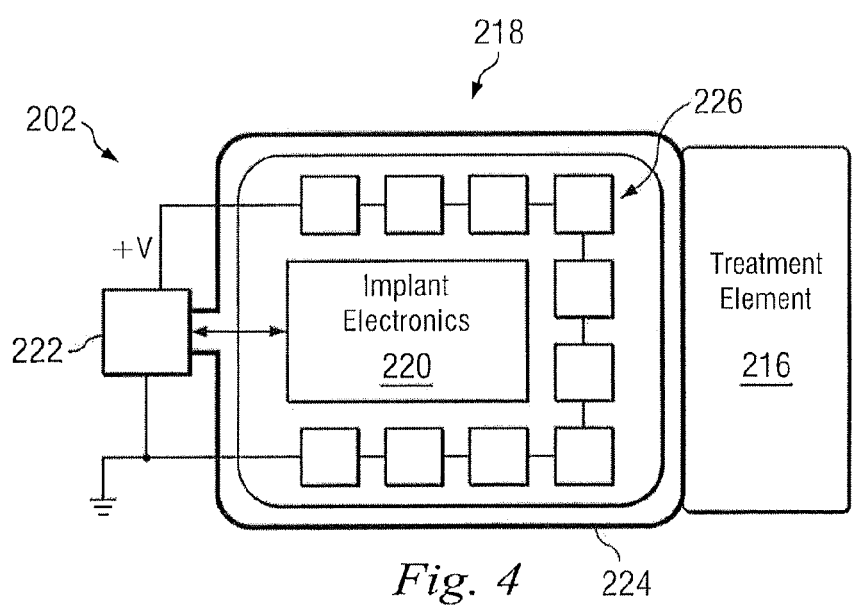
FIG. 4 is a schematic diagram of an implant of the ocular treatment system of FIG. 3 according to an exemplary embodiment of the present disclosure.

FIG. 4 shows an example of the implant 202 in greater detail. The implant 202 includes an electrically powered treatment element 216 and a power and control portion 218. The power and control portion 218 includes implant electronics 220, implant antenna management circuitry 222, an antenna 224 and an energy storage element 226. The treatment element 216 may be, for example, an electrically actuated valve, pump, injector, transducer or sensor, drug delivery element, or other monitoring or treatment device configured to treat a condition or monitor the status of the eye or any combination of these. It may also include for example telemetry, a data transmission module, or other element for communicating with the external unit 204.

The implant electronics 220 control the activity of the treatment element 216 by providing power, logic, control, or other electrical control contributions. In one example, the implant electronics 220 include a processor, such as an integrated circuit with power, input, and output pins capable of performing logic functions. In various embodiments, processor is a targeted device controller. In such a case, the processor is in communication with and performs specific control functions targeted to the treatment element 216. In other embodiments, the processor is a microprocessor programmable so that it can function to control the electrically powered treatment element 216. In other cases, the processor is a special purpose controller configured to control different aspects or functions of the implant 202. The implant electronics are in electrical communication with and receive power from the management circuitry. In some embodiments, this may include a processor or memory or may be a hard-coded memory.

The implant antenna management circuitry 222 includes filters and electrical circuitry components that power the implant electronics 220 and half duplex data. The implant antenna management circuitry 222 is in electrical communication with the implant electronics 220 and draws and passes power from the energy storage element 226 to the implant electronics 220.

In this example, the antenna 224 is a multi-turn loop antenna extending about or adjacent a peripheral portion of the power and control portion 218. The antenna 224 operates to receive excitation energy from the external unit 204 in a manner described below. Its electrical impedance is inductive and when placed within a flux field of the external unit 204, it behaves as a coil inductor and generates electrical energy. It may be a transducer or field to A/C converter. The antenna 224 may also be piezoelectric crystals, photovoltaics, and other energy capture systems that may capture power to operate the implant 202.

In the example shown, the energy storage element 226 is a parallel array of passive electrical components for storing energy, such as a parallel array of capacitors. However, the energy storage element 226 may be one or more of a combination of capacitors or array or capacitors, one or more batteries, or electromagnetic wave harvesters using the implant antenna 224.

As described above, the implant 202 is sized and arranged to be implanted on either a permanent or temporary basis into an eye. Therefore, some embodiments of the implant 202 are sized for example within the range smaller than about 16 mm×16 mm and preferably less than about 12 mm×12 mm and have a thickness less than about 3 mm and preferably less than about 2 mm thick. In one example, the implant has a thickness within the range of 1.5-2 mm. The implant 202 may be formed to the radius of the eye globe (about 0.5 inches). It may be rigid and preformed with a curvature suitable to substantially conform to the globe or it may be flexible and can flex to conform to the globe. Some implant embodiments are small enough that conforming to the globe provides little benefit in comfort or implantation technique.

The implant 202 may be positioned within the eye in the subconjunctival pocket between the conjunctiva and the sclera with the anterior border of the IOP control system 200 positioned slightly posterior to the limbus (the border between the cornea and the sclera). The implant 202 may be held in place within the eye via anchoring structures, the angle of implantation and surrounding anatomy, or by a spring force or other mechanisms that stabilize the implant 202.

Returning to FIG. 2, the external unit 204, in this exemplary embodiment includes a support structure 240, shown here as a pair of eyeglasses, a transmitter 242, and an attached power source 244. The transmitter 242 is arranged to emit an electromagnetic field and is particularly disposed on the support structure 240 at a location that transmits the electromagnetic field in a volume that captures or encompasses the implant 202. As such, the transmitter 242 may be disposed at a location suited for directing the electromagnetic field into a patient's eye. In this example, the transmitter 242 is carried on the support structure 240 at a location that places the transmitter 242 adjacent a patient's temple when wearing the support structure 240. In another example, the transmitter 242 is disposed on the eyeglasses support structure at the eyepiece. In one example, the transmitter is a solenoid having coils encircling an eyepiece of the eyeglasses, with the coils being embedded within or forming a frame.

Although shown here as a pair of eyeglasses, the support structure 240 could be any structure arranged to secure the transmitter 242 in a particular orientation relative to the implant 202. In one example, the support structure is a baseball cap with the transmitter 242 attached to the brim. Other examples include other types of hats, bonnets, hoods, head gear, ear-pieces, and others. Some examples of support structures are not worn, but are arranged to lie within charging range of the implanted implant. For example, the support structure may be associated with a pillow or pillow case arranged to charge the implant while the patient sleeps. Alternatively, it may be configured for attachment to a headboard, nightstand, or other furniture. In other examples, it is simply a housing that may help place the patient in a position, placing the implant proximate to the external unit for charging the implant.

The power source 244 is a rechargeable battery, such as a lithium ion or lithium polymer battery, although other types of batteries may be employed. In addition, any other type of power cell is appropriate for the power source 244. The power source 244 provides power to the transmitter 242, which in turn provides power to the implant 202. In this example, the power source may be placed apart from the transmitter 242, and is sized to fit within or be carried by a patient's pocket. In other examples, it may be sewn into the patient's hat or other location. In one example, the power source 244 is conventional electrical power from a power grid, such as may be accessed through a standard electrical outlet. This is particularly effective when the external unit 204 is a stationary system. The power source 244 in this example may be in communication with the transmitter via a wire or other electrical conductor.

Figure 5:
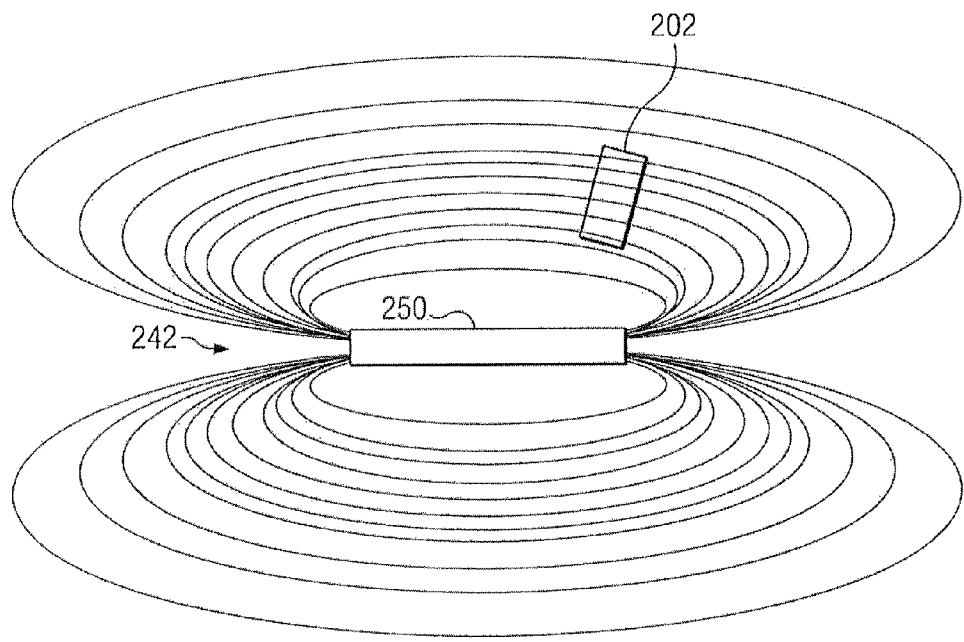
FIG. 5 is a schematic diagram of an electromagnetic flux field generated by a transmitter of the ocular treatment system of FIG. 2 according to an exemplary embodiment of the present disclosure.

FIG. 5 shows one example of the transmitter 242 and the implant 202, along with an exemplary flux or electromagnetic field generated by the transmitter 242. In this example, the transmitter 242 comprises a transmission antenna 250, which in this embodiment, may be a solenoid. As can be seen, by disposing the transmitter 242 at a suitable location relative to the implanted implant 202, the implant 202 is captured within the flux volume and can receive energy from the transmitter 242. The location of the transmitter 242 on the support structure 240 may be selected to provide the higher levels of flux, at a desired orientation, based on the expected orientation of the implant and the support structure 240. For example, the transmitter may be placed on the support structure at a location and orientation that causes electromagnetic flux emission direction to be transverse to the implant antenna 224 when the patient is looking forward, in an expected position. This may maximize the amount of flux captured by the antenna for powering the implant. The transmitter length, the permeability of the material the wires are wound on, and the relative position and angle of an implant antenna 224 on the implant 202 to the end of the transmitter 242 all affect the energy transfer efficiency to the implant 202.

FIG. 5 shows the transmission antenna 250 as a longitudinally extending body. In one example, the transmission antenna 250 is a cylindrically shaped body extending between a first end and a second end. The transmitted magnetic field flux density functions as a torus-shaped field with the transmission antenna 250 on axis. As can seen, considering the shape of the flux field, a large portion of the flux radiated from the transmitter 242 is not available to the implant 202.

Figure 6:
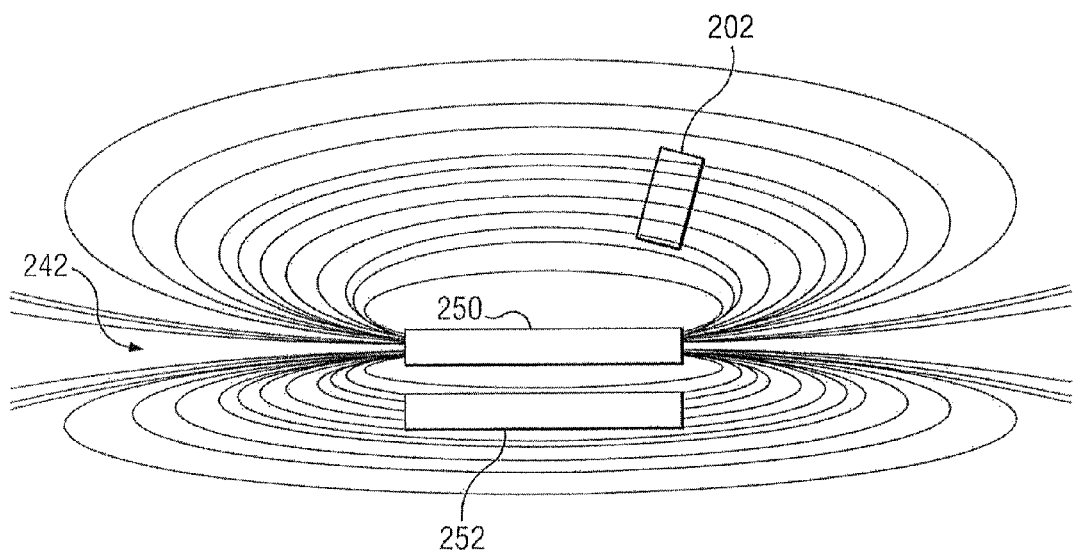
FIG. 6 is another schematic diagram of an electromagnetic flux field generated by a transmitter of the ocular treatment system of FIG. 2 according to another exemplary embodiment of the present disclosure.

An alternative embodiment of the transmitter 242 is shown in FIG. 6. The transmitter 242 in FIG. 6 comprises both the transmission antenna 250 and a flux-shunt 252 that directs the flux from the transmission antenna 250 more towards the implant 202. In this example, the flux-shunt 252 helps reduce flux transmitted to volumes not occupied by the implant 202. This may improve system electrical efficiency, reduce unintentional emissions, and enable multiple co-located systems to operate together with the least inter-patient RF interference. In addition, energy transmitted by the transmission antenna 250 that is more directed to the implant 202 may reduce or avoid capture effect by other nearby transponder units that may be on other implants. This may result in better transmission and less degradation that may arise from the implant being embedded in human conductive tissues.

Referring to FIG. 6, the flux shunt 252 is disposed adjacent to or in the flux volume generated by the transmission antenna 250 to limit or reduce the flux volume to undesired areas. Here, the flux shunt 252 is a low reluctance material disposed on a side of the transmission antenna 250 opposite the implant 202. In this example, the flux shunt 252 is a longitudinally extending element, having substantially the same length as the transmission antenna, arranged substantially parallel to the transmission antenna 250. As can be seen by the shape and density of the flux field in FIG. 6, the low reluctance flux shunt 252 reduces transmission into the unwanted volume surrounding the transmission antenna 250 by collecting most of the local flux and circulating it back to the transmission antenna 250. Since magnetic flux concentrates around the path of least resistance, placement of the low reluctance shunt 252 enables directional flux transmission.

In other embodiments however, the flux shunt 252 has a longitudinal length greater than the longitudinal length of the transmission antenna 250. Furthermore, in some embodiments, its shape different than that of the transmission antenna 250. Varying the shape, size, and orientation of the flux shunt 252 relative to the transmission antenna 250 provides directional control over the electromagnetic flux field emitted by the transmission antenna 250. As such, the field can be controlled to most effectively charge the implant in the most efficient manner.

In FIG. 6, the flux shunt 252 and the transmission antenna 250 provide more efficient transmission of the electromagnetic flux field to the implant 202 circuitry. The flux shunt 252 and transmission antenna 250 are small enough for installation on a wearable support structure 240 such as within an eyeglass design and with a flux field tailored for the application. That is, directing the flux field in a direction where the treatment implant 202 is expected to be located when the support structure 240 is in use. Applying the principles of magnetic circuits, it is possible to recirculate some of the flux in the transmission volume by shunting it back to the transmission antenna 250. Unlike unshunted flux, the re-circulated flux will not propagate to unintended directions. Provided that this magnetic shunt is low loss, the energy storage element properties of the transmission antenna 250 will be enhanced enabling fewer turns of wire and/or less excitation current to create the minimum required implant operational flux. The flux shunting technique can be used to shape the field contour density in three dimensions. Directing the flux using the flux shunt 252 provides improved system electrical efficiency, reduced undesirable radiation, and improved operation.

In one embodiment, the implant 202 includes a transmission device enabling it to broadcast information relating to the implant or the eye condition for consideration. For example, flow rates, pressures, charge status, and other conditions may be broadcast from the implant 202 for consideration by a surgeon or system to provide or achieve a desired treatment.

In use, a surgeon may implant the ocular implant 202 with its electrically powered treatment element, in the patient's eye to address an ocular condition. The implant 202 may draw power for operation from its energy storage element 226. The patient may wirelessly charge the energy storage element 226 or provide power to the implant 202 using the external unit 204 by generating an electromagnetic field that encompasses the implant 202. Generating the electromagnetic field may be accomplished by directing energy from the power source 244 to the transmission antenna 250, which may be a solenoid.

In one example, at least a portion of the external unit 204, such as the transmitter 242, is worn on a wearable support structure 240 about the face, such as eye-glasses, a cap, or other wearable elements, for example. As such, the transmitter 242 may be sized small enough to be comfortably carried on around a user's head and face. The location of the transmitter 242 is selected and designed to provide a desired flux volume at the desired orientation to the implant antenna 224. The transmitter 242 is then powered to emit the electromagnetic flux field.

In some embodiments, the direction of the electromagnetic field is controlled by locating the shunt 252 at a position within the electromagnetic field at a location opposite the desired transmission direction. For example, locating the shunt 252 may include locating the shunt so that the transmission antenna 250 is located in the area between the shunt 252 and the implant 202. As such, the electromagnetic field is stronger in the direction of the implant 202 than in the direction of the flux shunt 252.

Although described with reference to an intraocular implant and a transmitter, the flux shunting technique may have other applications beyond the intraocular implant. It may also be used with external units differing from the eyeglass temple antenna mount concept. Because ferrites are moldable and machinable on a custom basis, flux shunts may be used to direct flux in many ways and directions in addition to those disclosed herein.

Persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. A system for treating an ocular condition of a patient, comprising:
    an ocular implant sized for placement within an eye, the implant comprising:
    an electrically powered treatment element; and
    an antenna configured to receive energy for operating the electrically powered treatment element; and
    a wearable external system comprising:
    a transmitter sized to be carried on or adjacent the head of the patient for disposal adjacent the eye, the transmitter being arranged to emit an electromagnetic flux field to energize the antenna and provide power to operate the electrically powered treatment element of the implant, the transmitter comprising a transmission antenna that emits the electromagnetic flux field; and a flux shunt disposed within the electromagnetic flux field, the transmission antenna being disposed between the flux shunt and the implant; and
    a power source in communication with the transmitter and configured to provide power to the transmitter to emit the electromagnetic flux field.

2. The system of claim 1, wherein the flux shunt is cylindrically shaped and has a longitudinal axis extending in substantially the same direction as the transmitter.

3. The system of claim 1, wherein the implant comprises a rechargeable energy storage element, the electrically powered element being arranged to draw power from the energy storage element.

4. The system of claim 3, wherein the energy storage element comprises an array of storage elements arranged in parallel or series.

5. The system of claim 1, wherein the electrically powered treatment element comprises one of a valve and a pump.

6. The system of claim 1, wherein the implant is sized for placement into a subconjunctival pocket of the eye.

7. A system for treating an ocular condition of a patient, comprising:
    an electrically powered ocular implant sized for placement within an eye; and
    a transmitter sized to be carried on or adjacent the head of the patient for disposal adjacent the eye, the transmitter comprising:
    a transmission antenna that emits an electromagnetic flux field sufficient to energize the ocular implant; and a flux shunt disposed within the electromagnetic flux field, the transmission antenna being disposed between the flux shunt and the implant.

8. The system of claim 7, wherein the flux shunt is cylindrically shaped and has a longitudinal axis extending in substantially the same direction as the transmitter.

9. The system of claim 7, wherein the flux shunt is disposed at a location relative to the transmission antenna that reduces the electromagnetic flux field in a direction away from the ocular implant.

10. The system of claim 7, wherein the implant is sized for placement into a subconjunctival pocket of the eye.

11. The system of claim 7, comprising a power source in communication with the transmitter and configured to provide power to the transmitter to emit the electromagnetic flux field.

12. The system of claim 7, further comprising a support structure configured to place the implant within the electromagnetic flux of the transmitter.

13. The system of claim 12, wherein the support structure comprises one of eye-glasses and a hat.

14. The system of claim 7, wherein the implant is sized for placement into a subconjunctival pocket of the eye.

15. A method of powering an ocular implant sized for implantation in an eye of a patient comprising:
generating an electromagnetic flux field with a transmitter worn by the patient and disposed at a location relative to the ocular implant so that the electromagnetic flux field encompasses the implant;
limiting the electromagnetic flux field in a direction away from the implant in a manner that increases the electromagnetic flux field in a direction toward the implant; and
receiving energy at the implant from the electromagnetic flux field to power an electrically driven element on the implant to treat an ocular condition.

16. The method of claim 15, comprising storing the energy in an energy storage element.

17. The method of claim 15, wherein generating an electromagnetic flux field with a transmitter comprises generating the field with a transmission antenna, and wherein limiting the electromagnetic flux field in a direction away from the implant comprises locating a flux shunt at a side of the transmission antenna away from the implant.

18. A system for treating an ocular condition of a patient, comprising:
an ocular implant sized for placement within an eye, the implant comprising:
an electrically powered treatment element; and
an antenna configured to receive energy for operating the electrically powered treatment element; and
a wearable external system comprising:
a transmitter sized to be carried on or adjacent the head of the patient for disposal adjacent the eye, the transmitter being arranged to emit an electromagnetic flux field to energize the antenna and provide power to operate the electrically powered treatment element of the implant, wherein the transmitter is configured in a manner to provide a stronger electromagnetic flux field on one side than on the other, the stronger electromagnetic flux field being formed on the same side of the transmitter as the implant; and
a power source in communication with the transmitter and configured to provide power to the transmitter to emit the electromagnetic flux field.

19. A system for treating an ocular condition of a patient, comprising:
an ocular implant sized for placement within an eye, the implant comprising:
an electrically powered treatment element; and
an antenna configured to receive energy for operating the electrically powered treatment element; and
a wearable external system comprising:
a transmitter sized to be carried on or adjacent the head of the patient for disposal adjacent the eye, the transmitter being arranged to emit an electromagnetic flux field to energize the antenna and provide power to operate the electrically powered treatment element of the implant, wherein the transmitter comprises a transmission antenna having a first end and a second end, the transmission antenna being disposed on the wearable external system in a manner facing the implant, the implant antenna being disposed to be substantially transverse to the emission direction of the electromagnetic flux field; and
a power source in communication with the transmitter and configured to provide power to the transmitter to emit the electromagnetic flux field.

20. A system for treating an ocular condition of a patient, comprising:
an ocular implant sized for placement within an eye, the implant comprising:
an electrically powered treatment element;
a rechargeable energy storage element, the electrically powered element being arranged to draw power from the energy storage element, the energy storage element comprises an array of storage elements arranged in parallel or series; and
an antenna configured to receive energy for operating the electrically powered treatment element; and
a wearable external system comprising:
a transmitter sized to be carried on or adjacent the head of the patient for disposal adjacent the eye, the transmitter being arranged to emit an electromagnetic flux field to energize the antenna and provide power to operate the electrically powered treatment element of the implant; and
a power source in communication with the transmitter and configured to provide power to the transmitter to emit the electromagnetic flux field.

* * * * *